(12) United States Patent
Lin (10) Patent No.: US 6,789,540 B1
(45) Date of Patent: Sep. 14, 2004

(54) RESPIRATOR

(76) Inventor: Jung-Ming Lin, 6F, No. 35, Jen 3rd Rd., Keelung (TW)

(*) Notice: Subject to any disclaimer, the term of this patent is extended or adjusted under 35 U.S.C. 154(b) by 0 days.

(21) Appl. No.: 10/610,815

(22) Filed: Jul. 2, 2003

(51) Int. Cl.[7] ............................ A62B 7/00; A61M 16/00
(52) U.S. Cl. ............................ 128/205.19; 128/205.18; 128/205.24; 128/204.18; 128/204.21; 601/41; 601/43
(58) Field of Search .................. 128/205.13, 205.14, 128/205.16, 205.19, 205.24, 203.11, 202.28, 202.29, 204.18, 204.21; 601/41, 43, 133, 134, 135

(56) References Cited

U.S. PATENT DOCUMENTS

| | | | | |
|---|---|---|---|---|
| 1,371,702 A | * | 3/1921 | Lyon ..................... | 128/205.18 |
| 3,106,204 A | * | 10/1963 | Paramelle .............. | 128/205.16 |
| 3,216,413 A | * | 11/1965 | Andres .................. | 128/205.13 |
| 3,425,409 A | * | 2/1969 | Isaacson et al. ........ | 601/41 |
| 4,452,241 A | * | 6/1984 | Sarnoff et al. ......... | 128/204.18 |
| 4,934,360 A | * | 6/1990 | Heilbron et al. ....... | 128/205.16 |
| 4,971,053 A | * | 11/1990 | Tarrats .................. | 128/205.19 |
| 5,009,226 A | * | 4/1991 | Holt ...................... | 128/205.18 |
| 5,313,938 A | * | 5/1994 | Garfield et al. ........ | 128/205.16 |
| 5,345,929 A | * | 9/1994 | Jansson et al. ........ | 128/205.13 |
| 5,537,998 A | * | 7/1996 | Bauman ................ | 128/205.23 |
| 5,628,305 A | * | 5/1997 | Melker .................. | 128/202.29 |
| 5,711,295 A | * | 1/1998 | Harris, II ............... | 128/202.28 |
| 5,823,185 A | * | 10/1998 | Chang ................... | 128/204.18 |
| 6,397,843 B1 | * | 6/2002 | Tien-Tsai .............. | 128/204.18 |

* cited by examiner

*Primary Examiner*—Henry Bennett
*Assistant Examiner*—Mital Patel
(74) *Attorney, Agent, or Firm*—Troxell Law Office PLLC (57) ABSTRACT

A respirator includes a hollow body defining therein a fresh air body and an exhaust air body. The fresh air body includes a fresh air inlet and a first breathing pipe. The exhaust air chamber includes an exhaust air pipe and a second breathing pipe. A first piston is reciprocally received in the fresh air chamber and a second piston is reciprocally received in the exhaust air chamber so that fresh air is able to be forced to the mask and exhaust from the mask is able to be drawn from the mask and into the exhaust air chamber. A patient unable to breathe independently is forced to breathe by using the respirator.

17 Claims, 8 Drawing Sheets

RESPIRATOR

BACKGROUND OF THE INVENTION

1. Field of the Invention

The present invention relates to a respirator, and more particularly to a respirator which is able to force air into a victim's lungs and then suck the air out of the victim's lungs to compel the victim to breathe.

2. Description of Related Art

Figure 7:
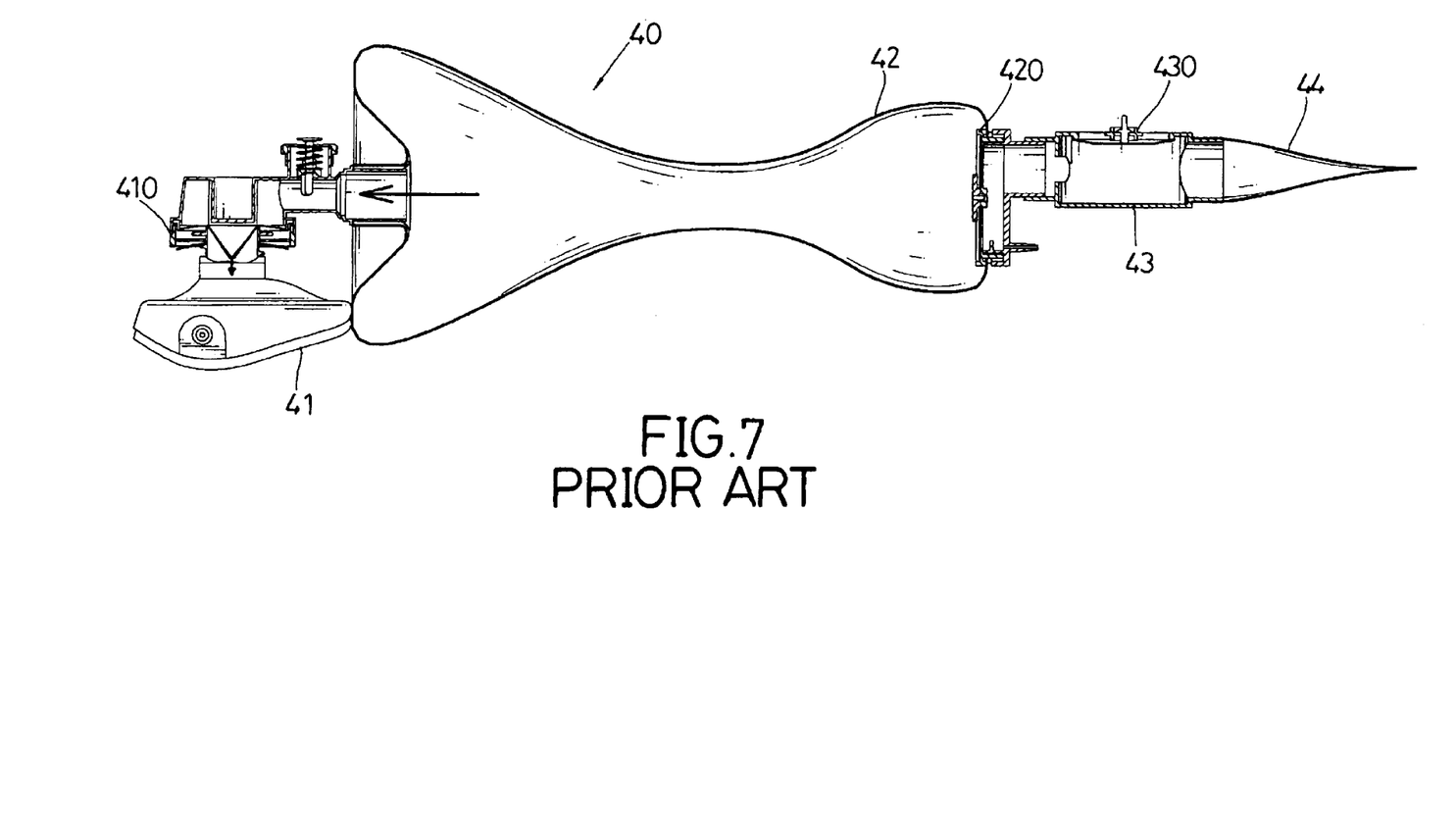
FIG. 7 is a side plan view showing the bulb of a conventional respirator being squeezed.
Figure 8:
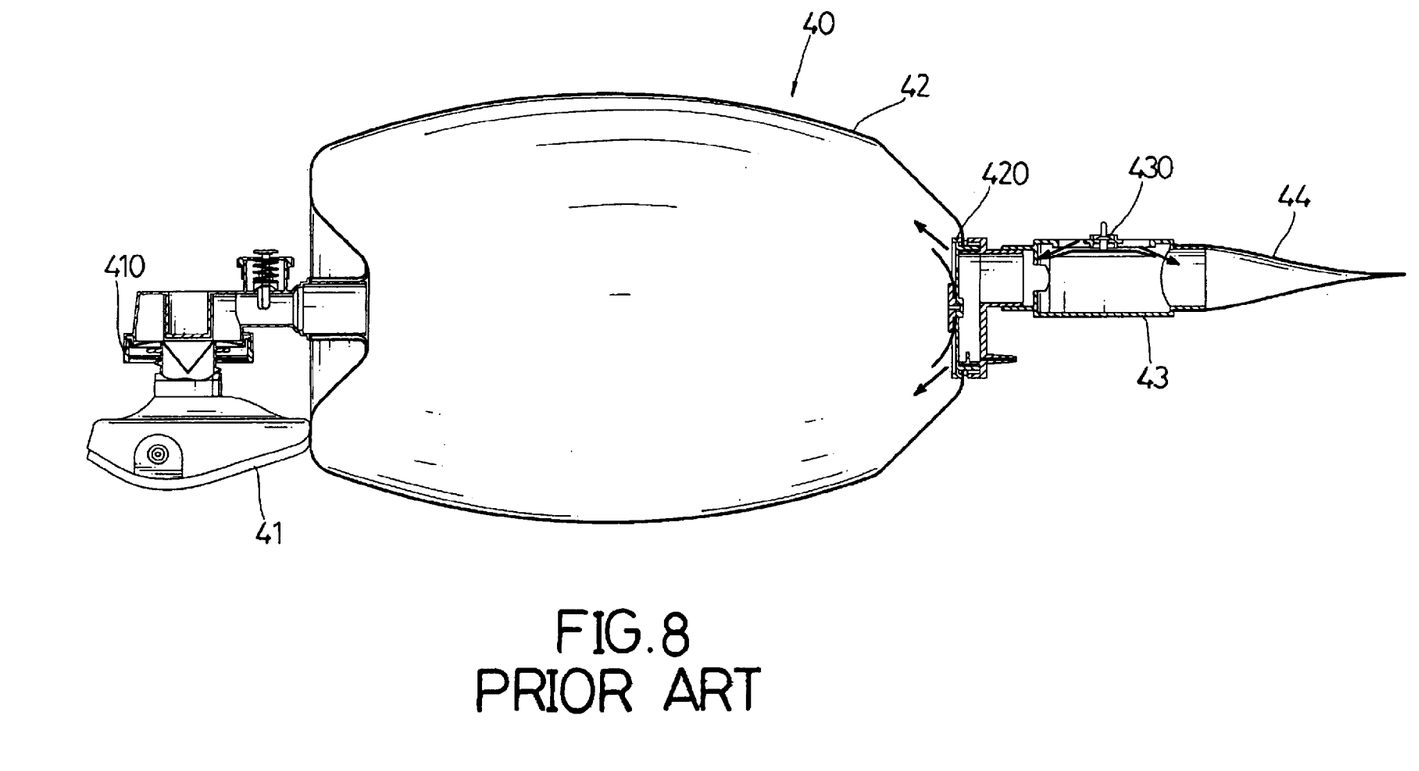
FIG. 8 is a side plan view showing the bulb in FIG. 7 is recovered.

With reference to FIGS. 7 and 8, a conventional respirator (40) includes a mask, a bulb (42), an intake control tube (43) and an air cell (44).

A first unidirectional valve (410) is provided between the mask (41) and the bulb (42) to prevent air from flowing back into the bulb (42) after the bulb (42) is squeezed. A second unidirectional valve (430) is provided between the air cell (44) and the bulb (42) to prevent air from flowing back into the air cell (44). Therefore, when the conventional respirator is in use, the user squeezes the bulb (42) to force air inside the bulb (42) to flow into the mask (41) via the first unidirectional valve (410). After the bulb (42) is squeezed, the resilience of the bulb (42) is able to facilitate the bulb (42) to restore its original shape by sucking air into the bulb (42) via the second unidirectional valve (430).

When this conventional respirator is in use, although the air is able to be continuously forced into a victim's lungs, there is no mechanism to dissipate exhaust air from the victim's lungs. That is, the paramedic has to wait for the victim's intercostal muscles to relax to proceed pumping the air into the victim's lungs. Another risk of using this conventional respirator is that if there is phlegm in the victim's airway, the phlegm will be pushed deeper and deeper into the lungs everytime the air is forced into the mask (41). It is common knowledge that the phlegm will eventually block the victim's airway and cause suffocation if the phlegm is not properly removed from the victim.

To overcome the shortcomings, the present invention tends to provide an improved respirator to mitigate the aforementioned problems.

SUMMARY OF THE INVENTION

The primary objective of the present invention is to provide an improved respirator having a fresh air chamber, an exhaust air chamber and a piston mechanism with a first piston reciprocally received in the fresh air chamber and a second piston reciprocally received in the exhaust air chamber so that when the piston mechanism is actuated by a power source, the reciprocal movement of the fresh air chamber is able to continuously force fresh air into the mask and the reciprocal movement of the second piston is able to suck exhaust air from the victim via the mask.

Another objective of the present invention is that the fresh air chamber is in series with the exhaust air chamber and the piston mechanism has a piston rod extending through the exhaust air chamber and the into the fresh air chamber.

Still another objective of the invention is that the fresh air chamber is parallel with the exhaust air chamber and the piston mechanism has a first piston rod connected to the first piston and a second piston rod connected to the second piston such that the respective movement of the first piston rod and the second piston rod is able to force air into and out of the victim's body to compel the victim to repeat contraction and release of intercostal muscle.

Other objects, advantages and novel features of the invention will become more apparent from the following detailed description when taken in conjunction with the accompanying drawings.

DETAILED DESCRIPTION OF THE PREFERRED EMBODIMENT

Figure 1:
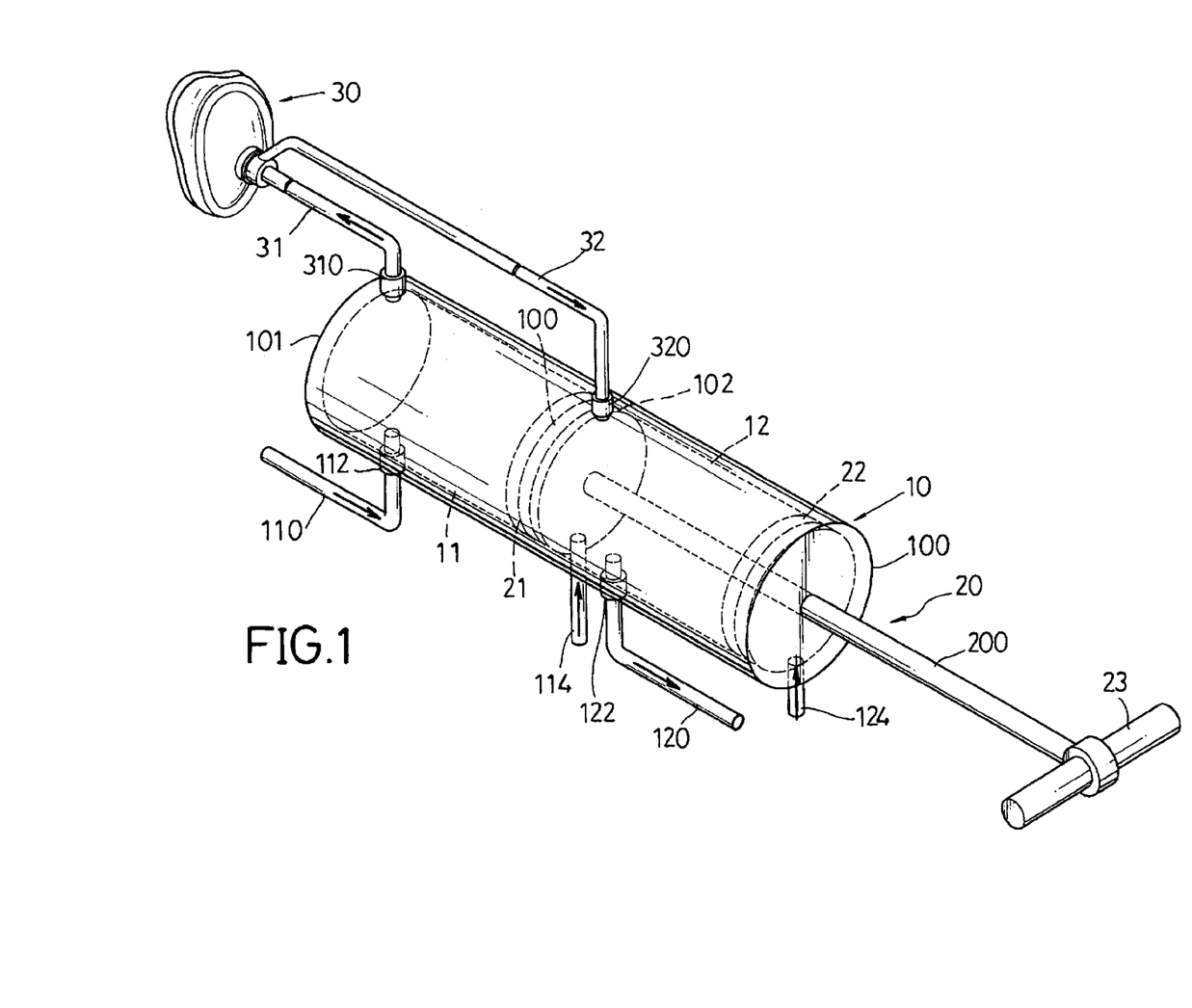
FIG. 1 is a perspective view of the first preferred embodiment of the present invention

With reference to FIG. 1, the respirator in accordance with the present invention includes a hollow body (10), a piston mechanism (20) and a mask (30).

The hollow body (10) is divided into a fresh air body (11) and an exhaust air chamber (12) by a baffle (102) securely formed inside the hollow body (10). The hollow body (10) has an assembly end (100) and a closed end (101). The fresh air chamber (11) is provided with a first fresh air inlet (110) communicating with the fresh air chamber (11) and the exhaust air chamber (12) has a second fresh air inlet (114) communicating with the exhaust air chamber (12). The exhaust air chamber (12) further has an exhaust pipe (120) communicating with the surrounding air and a pressure balance pipe (124) formed near the assembly end (100) of the hollow body (10) to communicate the exhaust air chamber (12) with the surrounding air atmosphere.

The piston mechanism (20) has a piston rod (200) extending through the exhaust air chamber (12) and into the fresh air chamber (11), a first piston (21) securely mounted on a first distal end of the piston rod (200) and reciprocally received inside the fresh air chamber (11) and a second piston (22) securely mounted on a mediate portion of the piston rod (200) and reciprocally received inside the exhaust air chamber (12) and a handle (23) formed on a second distal end of the piston rod (200) opposite to the first distal end of the piston rod (200).

The mask (30) has an air inlet pipe (31) connected to and communicated with the fresh air chamber (11) and an exhaust air pipe (32) connected to and communicated with the exhaust air chamber (12).

The fresh air inlet (110) has a first unidirectional valve (112) mounted inside the fresh air inlet (110) to allow fresh air to flow only into the fresh air chamber (11). The exhaust pipe (120) has a second unidirectional valve (122) to allow the air inside the exhaust air chamber (12) to flow only out of the exhaust air chamber (12). The air inlet pipe (31) has a third unidirectional valve (310) to allow the fresh air from the fresh air chamber (11) to flow only into the mask (30) and the exhaust air pipe (32) has a fourth unidirectional valve (320) mounted inside the exhaust air pipe (32) to allow the exhaust air from the mask (30) to flow only into the exhaust air chamber (12).

Figure 2:
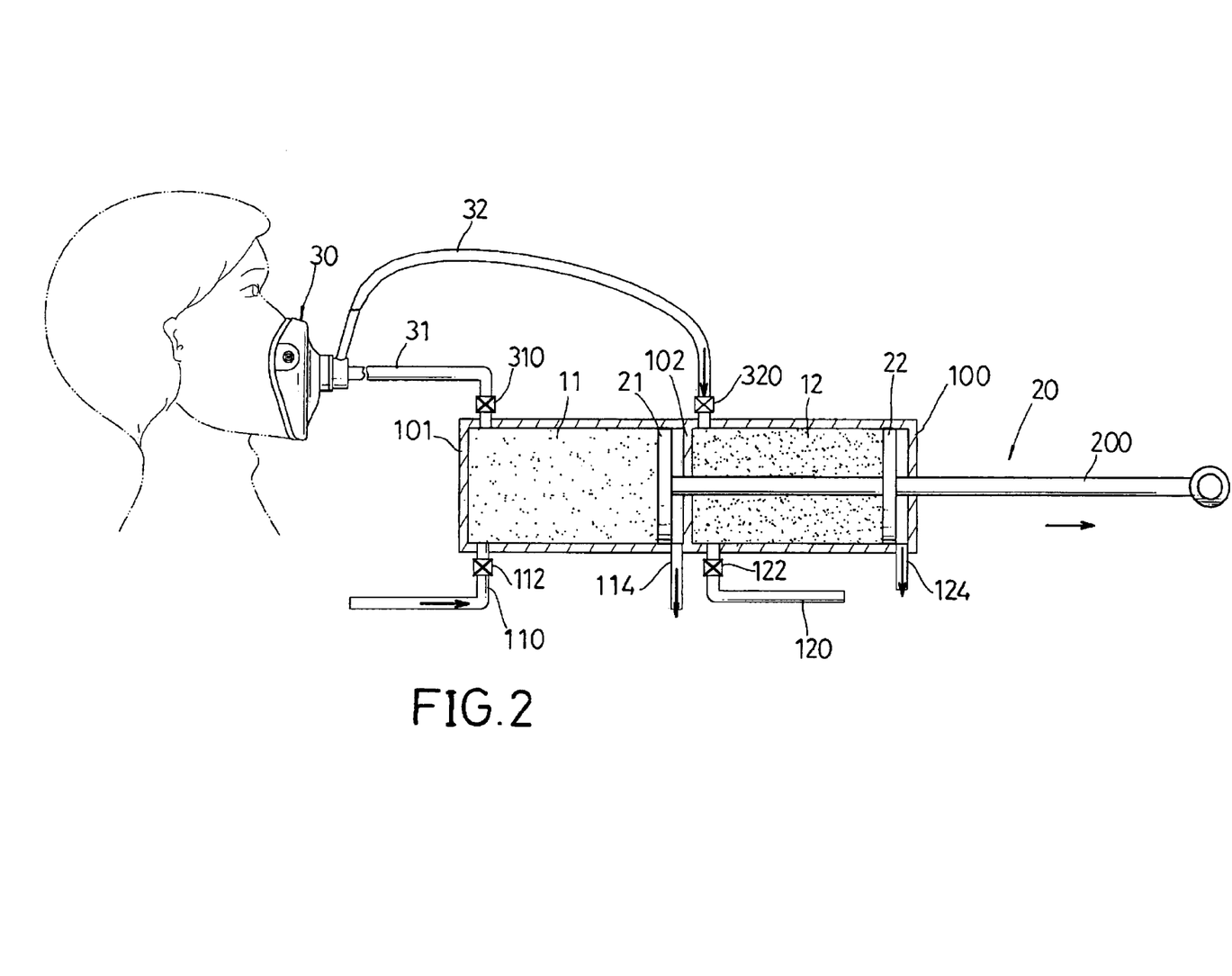
FIG. 2 is a schematic side plan view showing the application of the first embodiment.

With reference to FIG. 2, when the respirator of the present invention is in application, the mask (30) is applied to cover the patient's nose and mouth. Then the operator (the paramedic) operates the piston rod (200) by holding the handle (23). When the first piston (21) and the second piston (22) are moved toward the closed end (101) of the hollow body (10), the air inside the fresh air chamber (11) is forced to flow to the air inlet pipe (31) and into the mask (30) for the patient. Meanwhile, the air inside the exhaust air chamber (12) is forced out of the exhaust air chamber (12) via the exhaust pipe (120). When the first and second piston (21,22) are moved toward the assembly end (100), fresh air is sucked into the fresh air chamber (11) via the fresh air inlet (110) and exhaust air from the patient is sucked into the exhaust air chamber (12) via the exhaust air pipe (32). Therefore, the repetition movement of the piston rod (200) forces fresh air into the mask (30) and sucks exhaust air from the mask (30) when the mask (30) is applied on the face of a patient. Furthermore, the movement of the second piston (22) forces the intercostal muscle to release to accomplish the purpose to force the patient to breathe.

Figure 3:
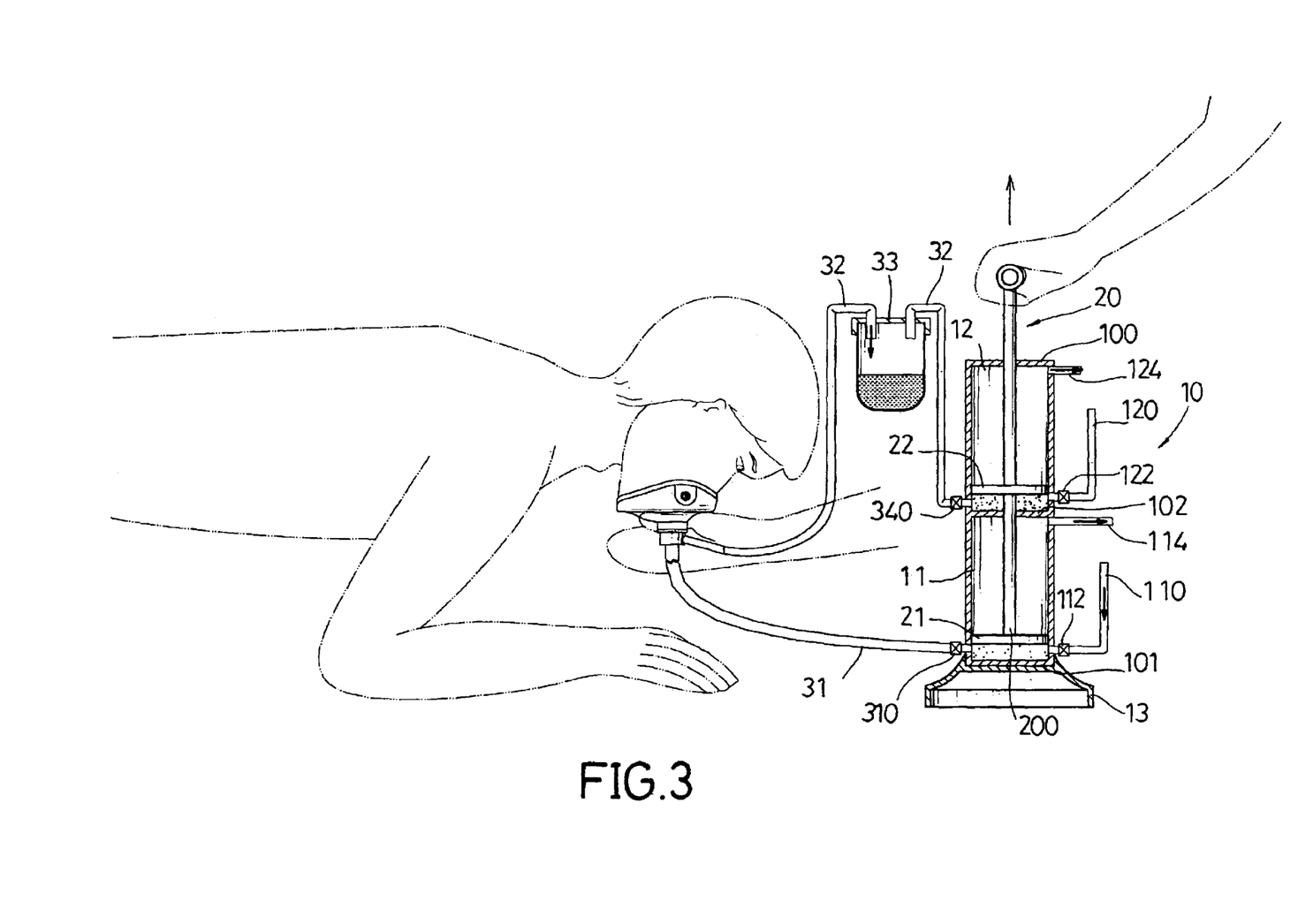
FIG. 3 is a schematic side plan view showing another application of the first embodiment.

With reference to FIG. 3, when the patient is injured to the extent of not being suitable for movement, a conventional respirator requires the patient to lie on his/her back, which is very dangerous for the patient as possible required movement may be disastrous. However, when applying the respirator of the present invention, it is noted that the respirator of the present invention does not require the patient to lie face upward. Thus, the respirator is especially useful for an injured person lying face down and not suitable for any movement.

Furthermore, the respirator of this preferred embodiment may further include a phlegm container (33) provided in any portion of the exhaust air pipe (32). That is, the phlegm container (33) is provided between the mask (30) and the exhaust air chamber (12) Thus, when the second piston (22) is move toward to the assembly end (100), the suction force inside the exhaust air pipe (32) may suck phlegm out of the patient's throat. When the phlegm passes the phlegm container (33), the phlegm may drop into the phlegm container (33) due to gravity effect.

Figure 4:
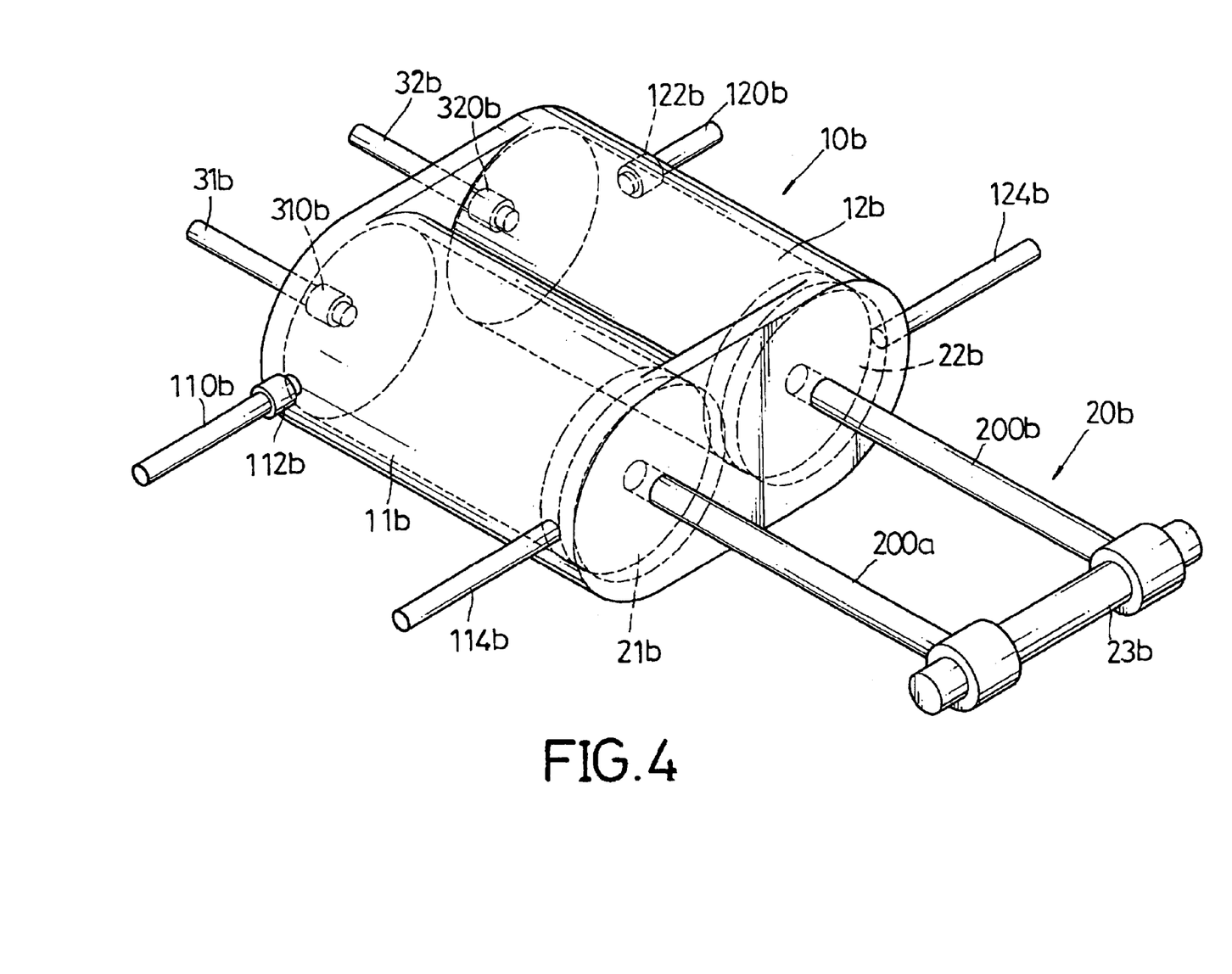
FIG. 4 is a perspective view of the second preferred embodiment of the present invention.
Figure 5:
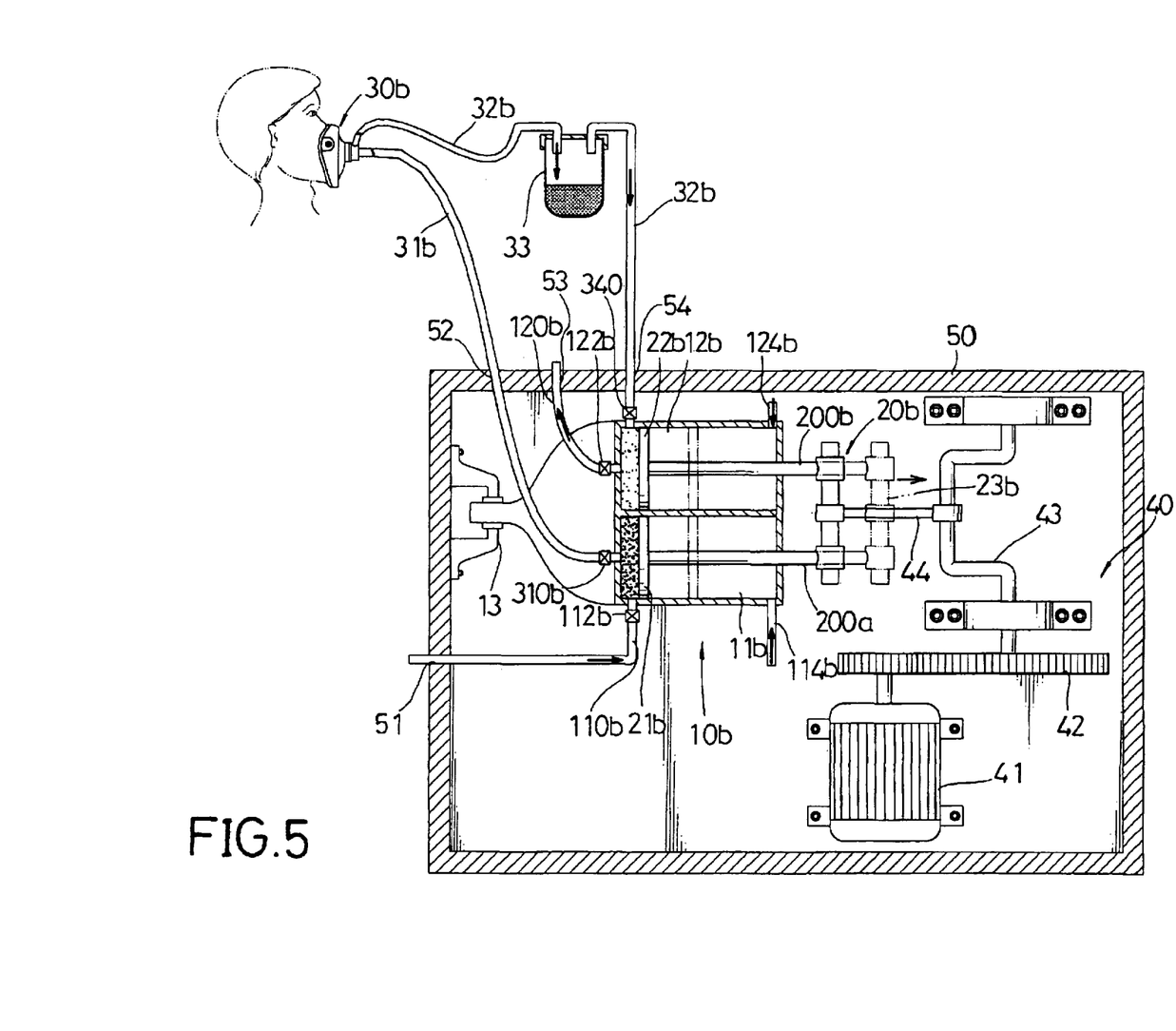
FIG. 5 is a schematic side plan view of the second embodiment.

With reference to FIGS. 4 and 5, another preferred embodiment of the present invention is shown and the respirator of the present invention includes a hollow body (10b), a piston mechanism (20b) and a mask (30b).

The hollow body (10b) is provided with a fresh air body (11b) and an exhaust air chamber (12b) parallel with the fresh air chamber (11b). The fresh air chamber (11b) is provided with a fresh air inlet (110b) communicating with the fresh air chamber (11b) and a first breathing pipe (114b) communicating the interior of the fresh air chamber (11b) with the surrounding air. The exhaust air chamber (12b) has an exhaust pipe (120b) communicating the interior of the exhaust air chamber (12b) with the surrounding air and a second breathing pipe (124b) communicating with the exhaust air chamber (12b).

The piston mechanism (20b) has a first piston rod (200a) extending into the fresh air chamber (11b) and having a first piston (21b) securely mounted on a first distal end of the first piston rod (200a) and reciprocally received inside the fresh air chamber (11b) and a second piston rod (200b) extending into the exhaust air chamber (12b) and having a second piston (22b) securely mounted on a first distal end of the second piston rod (200b) and reciprocally received inside the exhaust air chamber (12b). Second distal ends of the first piston rod (200a) and the second piston rod (200b) are connected to a handle (23b). The mask (30b) includes an air inlet pipe (31b) communicating the mask (30b) with the interior of the fresh air chamber (11b) and an exhaust air pipe (32b) communicating the mask (30b) with the exhaust air chamber (12b).

The fresh air inlet (110b) has a first unidirectional valve (112b) mounted inside the fresh air inlet (110b) to allow fresh air from the surroundings to flow only into the interior of the fresh air chamber (11b). The exhaust air chamber (12b) has a second unidirectional valve (122b) mounted inside the exhaust air chamber (12b) to allow air inside the exhaust air chamber (12b) to flow only out of the exhaust air chamber (12b). The air inlet pipe (31b) has a third unidirectional valve (310b) mounted inside the air inlet pipe (31b) to allow fresh air from the fresh air chamber (11b) to flow only into the mask (30b). The exhaust air pipe (32b) has a fourth unidirectional valve (320b) mounted inside the exhaust air pipe (32b) to allow air from the mask (30b) to flow only into the exhaust air chamber (12b).

With reference to FIG. 5, it is noted that the preferred embodiment of the respirator of the present invention may use a transmission device (40) as a power source to drive the handle (23b) to move reciprocally. The transmission device (40) is enclosed inside a casing (50) which has a first hole (51) defined to correspond to the fresh air inlet (110b), a second hole (52) defined to correspond to the air inlet pipe (31b), a third hole (53) defined to correspond to the exhaust air pipe (53) and a fourth hole (54) defined to correspond to the exhaust air pipe (32b).

In order to securely position the hollow body (10b) inside the casing (50), the hollow body (10b) has a bracket (13) formed at a front side of the hollow body (10b) and securely connected to an inner side face of the casing (50).

The transmission device (40) has a motor (41), a transmission gear (42) driven by the motor (41), a transmission rod (43) rotatably received inside the casing (50) and driven by the transmission gear (42) and a connection rod (44) connected between the handle (23b) and the transmission rod (43). The transmission rod (43) is substantially a U shape such that when the transmission rod (43) is driven by the transmission gear (42), the rotation of the transmission rod (43) drives the connection rod (44) to move linearly, which drives the handle (23b) to move accordingly.

Figure 6:
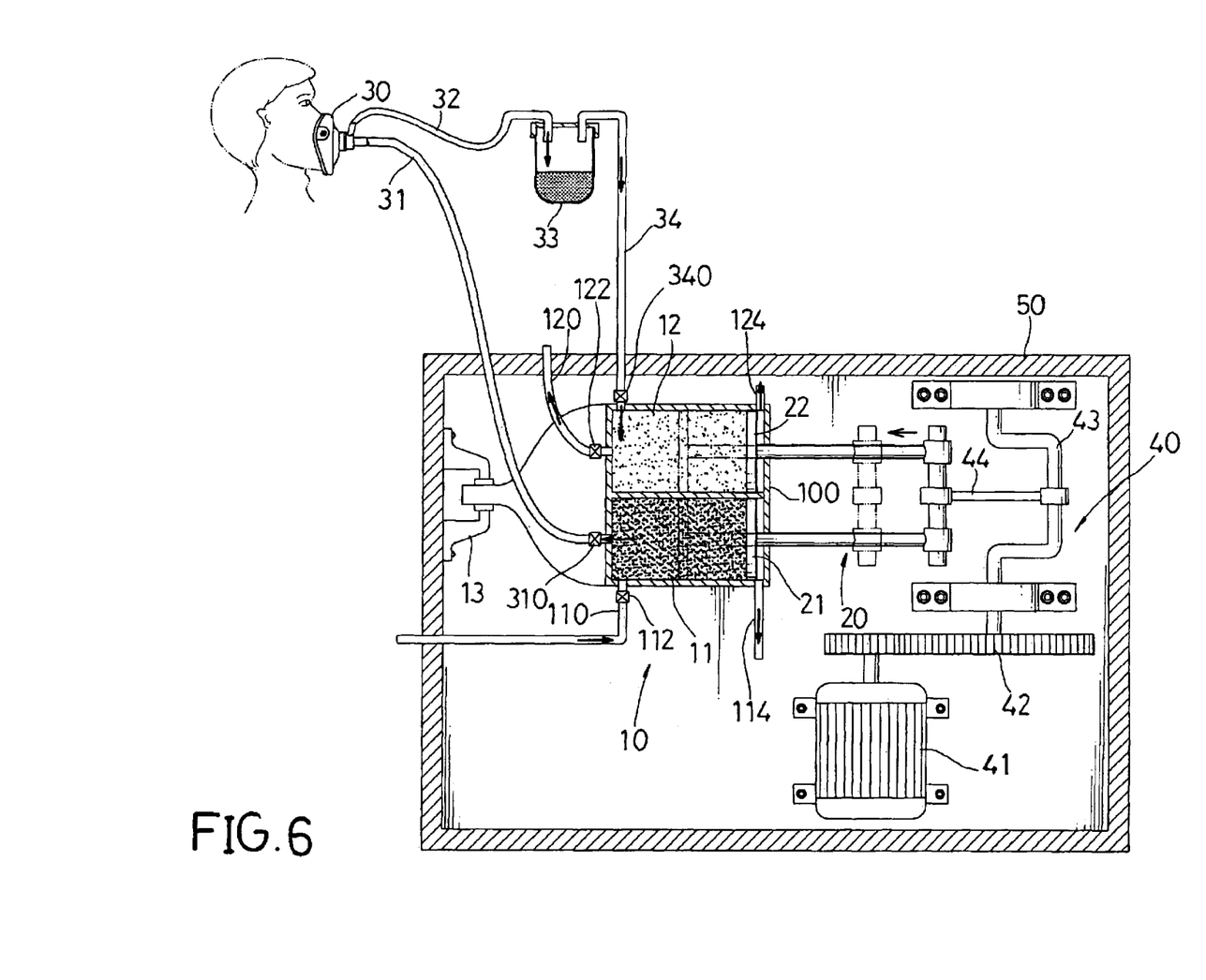
FIG. 6 is a schematic side plan view showing the movement of the piston mechanism is driven by the motor to cause fresh air to be sucked into the fresh air chamber and the exhaust air to be sucked out of the victim via the mask.

With reference to FIG. 6 and taking FIG. 5 for comparison, it is to be noted that when the motor (41) is initiated, the transmission gear (42) drives the transmission rod (43) to rotate. The rotation of the transmission rod (43) drives the connection rod (44) to thus move linearly. The linear movement of the connection rod (44) drives the handle (23b) to move reciprocally accordingly. When the first piston (21b) is moved to force the air inside the fresh air chamber (11b) to flow into the air inlet pipe (31b), the second piston (22b) also move to force the air inside the exhaust air chamber (12b) to flow out of the exhaust air chamber (12b) via the exhaust pipe (120b). Meanwhile, in order to maintain the smooth movement of the first piston (21b) and the second piston (22b), the first and second breathing pipes (114b,124b) suck air from the interior of the casing (50) into the fresh air chamber (11b) and the exhaust air chamber (12b) respectively. The air flowing out of the fresh air chamber (11b) flows to the mask (30b) via the control of the third unidirectional valve (310b). The air flowing out of the exhaust air chamber (12b) flows out of the casing (50) via the control of the fourth unidirectional valve (320b).

When the first and second pistons (21b,22b) are moved by the rotational movement of the transmission rod (43), exhaust air from the mask (30b) is drawn from the mask (30b) via the exhaust air pipe (32b) to the exhaust air chamber (12b). It is to be noted that a phlegm container (33) may be provided in any portion in the exhaust air pipe (32b) so that when the exhaust air is drawn from the mask (30b), if there is phlegm contained in the exhaust air from the mask (30b), the phlegm is able to be collected by the phlegm container (33) due to gravity effect on the phlegm. When the exhaust air chamber (12b) is full of exhaust air, the reciprocal movement of the second piston (22b) forces the exhaust air out of the casing (50) via the exhaust pipe (120b) to complete the cycle.

Thus, it is noted that the respirator of the present invention is able to force the patient to breathe, not only to inhale but also to exhale, which is very helpful to a patient who has lost the ability to breathe independently.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the fill extent indicated by the broad general meaning of the terms in which the appended claims are expressed.

What is claimed is:

1. A respirator comprising:
   a hollow body having a closed end and an assembly end and defining therein a fresh air chamber and an exhaust air chamber, wherein the fresh air chamber has a fresh air inlet formed close to a first end inside the fresh air chamber to communicate the fresh air chamber with surrounding air and provided with a first unidirectional valve to allow air from the surrounding air to flow only into the fresh air chamber and a first breathing pipe formed close to a second end inside the fresh air chamber to communicate the fresh air chamber with the surrounding air, the exhaust air chamber has an exhaust pipe formed close to a first end inside the exhaust air chamber to communicate the exhaust air chamber with surrounding air and provided with a second unidirectional valve to allow air from the exhaust air chamber to flow only out of the exhaust air chamber and a second breathing pipe formed close to a second end inside the exhaust air chamber to communicate the exhaust air chamber with the surrounding air;
   a mask having an air inlet pipe communicating the interior of the fresh air chamber with the mask and provided with a third unidirectional valve to allow the air from the fresh air chamber to flow only to the mask and an exhaust air pipe communicating the interior of the exhaust air chamber with the mask and provided with a fourth unidirectional valve to allow air from the mask to flow only to the exhaust air;
   a piston mechanism having a first piston reciprocally received in the fresh air chamber to intermittently force the air inside the fresh air chamber to the mask via the air inlet pipe and a second piston reciprocally received in the exhaust air chamber to intermittently force the air inside the exhaust air chamber out to surroundings;
   a handle operably connected to the first piston and the second piston; and
   means for driving the handle to move linearly so as to drive the first piston and the second piston to move simultaneously inside the fresh air chamber and the exhaust air chamber respectively.

2. The respirator as claimed in claim 1, wherein the fresh air chamber is in series with the exhaust air chamber and a baffle is formed between the fresh air chamber and the exhaust air chamber.

3. The respirator as claimed in claim 2 further comprising a phlegm container provided in the exhaust air pipe such that phlegm in the air flowing into the exhaust air chamber is collected by the phlegm container.

4. The respirator as claimed in claim 3, wherein the piston mechanism includes a piston rod extending into the exhaust air chamber and the fresh air chamber, the first piston is securely mounted on a first distal end of the piston rod extending into the fresh air chamber and the second piston is securely mounted at a mediate portion of the piston rod such that movement of the first piston and the second piston is simultaneous.

5. The respirator as claimed in claim 2, wherein the piston mechanism includes a piston rod extending into the exhaust air chamber and the fresh air chamber, the first piston is securely mounted on a first distal end of the piston rod extending into the fresh air chamber and the second piston is securely mounted at a mediate portion of the piston rod such that movement of the first piston and movement of the second piston are simultaneous.

6. The respirator as claimed in claim 1 further comprising a phlegm container provided in the exhaust air pipe such that phlegm in the air flowing into the exhaust air chamber is collected by the phlegm container.

7. The respirator as claimed in claim 1, wherein the means comprises a motor, a transmission gear driven by the motor, a transmission rod driven by the transmission gear to rotate and a connection rod connected between the transmission rod and the handle such that the rotation of the transmission rod is able to drive the piston mechanism to move linearly.

8. The respirator as claimed in claim 7, wherein the means further comprises a casing to enclose the hollow body, the casing having a first hole corresponding to the fresh air inlet, a second hole corresponding to the air inlet pipe, a third hole corresponding to the exhaust air pipe and a fourth hole corresponding to the exhaust pipe, wherein the hollow body having a bracket securely connected to an inner side face of the casing to position the hollow body inside the casing.

9. The respirator as claimed in claim 8, wherein the transmission rod is U-shaped.

10. The respirator as claimed in claim 1, wherein the fresh air chamber is parallel with the exhaust air chamber.

11. The respirator as claimed in claim 10, wherein the piston mechanism includes a first piston rod extending into the fresh air chamber to have the first piston to be mounted at a first distal end of the first piston rod and a second piston rod extending into the exhaust air chamber to have the second piston securely mounted at a first distal end of the second piston rod, the first piston rod and the second piston rod are connected to the handle.

12. The respirator as claimed in claim 11 further comprising a phlegm container provided in the exhaust air pipe such that phlegm in the air flowing into the exhaust air chamber is collected by the phlegm container.

13. The respirator as claimed in claim 10 further comprising a phlegm container provided in the exhaust air pipe such that phlegm in the air flowing into the exhaust air chamber is collected by the phlegm container.

14. The respirator as claimed in claim 10, wherein the means comprises a motor, a transmission gear driven by the motor, a transmission rod driven by the transmission gear to rotate and a connection rod connected between the transmission rod and the handle such that the rotation of the transmission rod is able to drive the piston mechanism to move linearly.

15. The respirator as claimed in claim 14, wherein the means further comprises a casing to enclose the hollow body, the casing having a first hole corresponding to the fresh air inlet, a second hole corresponding to the air inlet pipe, a third hole corresponding to the exhaust air pipe and a fourth hole corresponding to the exhaust pipe, wherein the hollow body having a bracket securely connected to an inner side face of the casing to position the hollow body inside the casing.

16. The respirator as claimed in claim 15, wherein the transmission rod is U-shaped.

17. A respirator comprising:

a hollow body having a closed end and an assembly end and defining therein a fresh air chamber and an exhaust air chamber, wherein the fresh air chamber has a fresh air inlet formed close to a first end inside the fresh air chamber to communicate the fresh air chamber with surrounding air and :provided with a first unidirectional valve to allow air from the surrounding air to flow only into the fresh air chamber and a first breathing pipe formed close to a second end inside the fresh air chamber to communicate the fresh air chamber with the surrounding air, the exhaust air chamber has an exhaust pipe formed close to a first end inside the exhaust air chamber to communicate the exhaust air chamber with surrounding air and provided with a second unidirectional valve to allow air from the exhaust air chamber to flow only out of the exhaust air chamber and a second breathing pipe formed close to a second end inside the exhaust air chamber to communicate the exhaust air chamber with the surrounding air;

a mask having an air inlet pipe communicating the interior of the fresh air chamber with the mask and provided with a third unidirectional valve to allow the air from the fresh air chamber to flow only to the mask and an exhaust air pipe communicating the interior of the exhaust air chamber with the mask and provided with a fourth unidirectional valve to allow air from the mask to flow only to the exhaust air;

a piston mechanism having a first piston reciprocally received in the fresh air chamber to intermittently force the air inside the fresh air chamber to the mask via the air inlet pipe and a second piston reciprocally received in the exhaust air chamber to intermittently force the air inside the exhaust air chamber out to surroundings;

a phlegm container provided in the exhaust air pipe such that phlegm in the air flowing into the exhaust air chamber is collected by the phlegm container;

a handle operably connected to the first piston and the second piston; and means for driving the handle to move linearly so as to drive the first piston and the second piston to move simultaneously inside the fresh air chamber and the exhaust air chamber respectively, wherein the fresh air chamber is parallel with the exhaust air chamber, wherein the piston mechanism includes a first piston rod extending into the fresh air chamber to have the first piston mounted at a first distal end of the first piston rod and a second piston rod extending into the exhaust air chamber to have the second piston securely mounted at a first distal end of the second piston rod, the first piston rod and the second piston rod are connected to the handle, wherein the means comprises a motor, a transmission gear driven by the motor, a transmission rod driven by the transmission gear to rotate, a connection rod connected between the transmission rod and the handle such that the rotation of the transmission rod is able to drive the piston mechanism to move linearly and a casing to enclose the hollow body, the casing having a first hole corresponding to the fresh air inlet, a second hole corresponding to the air inlet pipe, a third hole corresponding to the exhaust air pipe and a fourth hole corresponding to the exhaust pipe, wherein the hollow body having a bracket securely connected to an inner side face of the casing to position the hollow body inside the casing, wherein the transmission rod is U-shaped.

* * * * *